United States Patent [19]

Kavaya

[11] 4,253,769
[45] Mar. 3, 1981

[54] STARK EFFECT SPECTROPHONE FOR CONTINUOUS ABSORPTION SPECTRA MONITORING

[76] Inventor: Robert A. Frosch, Administrator of the National Aeronautics and Space Administration, with respect to an invention of Michael J. Kavaya, San Gabriel, Calif.

[21] Appl. No.: 154,726

[22] Filed: May 30, 1980

[51] Int. Cl.³ .............................................. G01J 1/00
[52] U.S. Cl. .................................. 356/432; 250/350
[58] Field of Search ................ 356/432, 435; 250/343, 250/349, 350, 340

[56] References Cited

U.S. PATENT DOCUMENTS

| | | | |
|---|---|---|---|
| 3,921,099 | 11/1975 | Abrams et al. | 331/94.55 |
| 4,068,125 | 1/1978 | Bell | 250/343 |
| 4,105,919 | 8/1978 | Bridges et al. | 250/341 |

*Primary Examiner*—R. A. Rosenberger
*Attorney, Agent, or Firm*—Monte F. Mott; John R. Manning; Paul F. McCaul

[57] ABSTRACT

A Stark effect spectrophone is provided using a pulsed or continuous wave laser (33) having a beam with one or more absorption lines of a constituent of an unknown gas. The laser beam is directed through windows (31,032) of a closed cell (30) while the unknown gas to be monitored is caused to flow continuously through the cell between electric field plates (34, 35) disposed in the cell on opposite sides of the beam path through the cell. The plates are so disposed as to be divergent, e.g., flat plates at an oblique angle relative to each other, or plates shaped according to a mathematical function so that, with constant voltage applied across the plates, there is a linear variation in electric field strength along the beam path. Discrete pressure transducers (37) are positioned at field strength points of interest. When the beam is pulsed, energy absorbed by the gas then present in the cell will increase at each point along the beam path according to the spectral lines of the constituents of the gas for the particular field strengths at those points. The pressure measurement at each point during each pulse of energy will yield a plot of absorption as a function of electric field for simultaneous detection of the gas constituents of interest. Signal averagers (39) are provided to permit repeatedly pulsing the laser for averaging before recording and processing the data. When the beam is continuous (i.e., not pulsed), the bias voltage may be modulated to dither the electric field at each point. Still other techniques that may be used for modulation of the absorbed energy include polarization rotation, wavelength modulation and conventional 50% duty cycle chopping of the incident beam.

10 Claims, 5 Drawing Figures

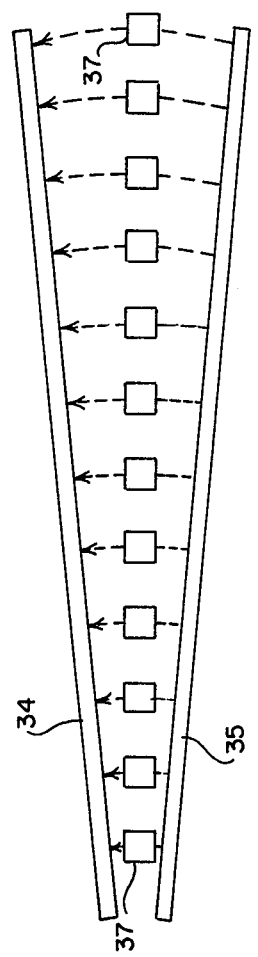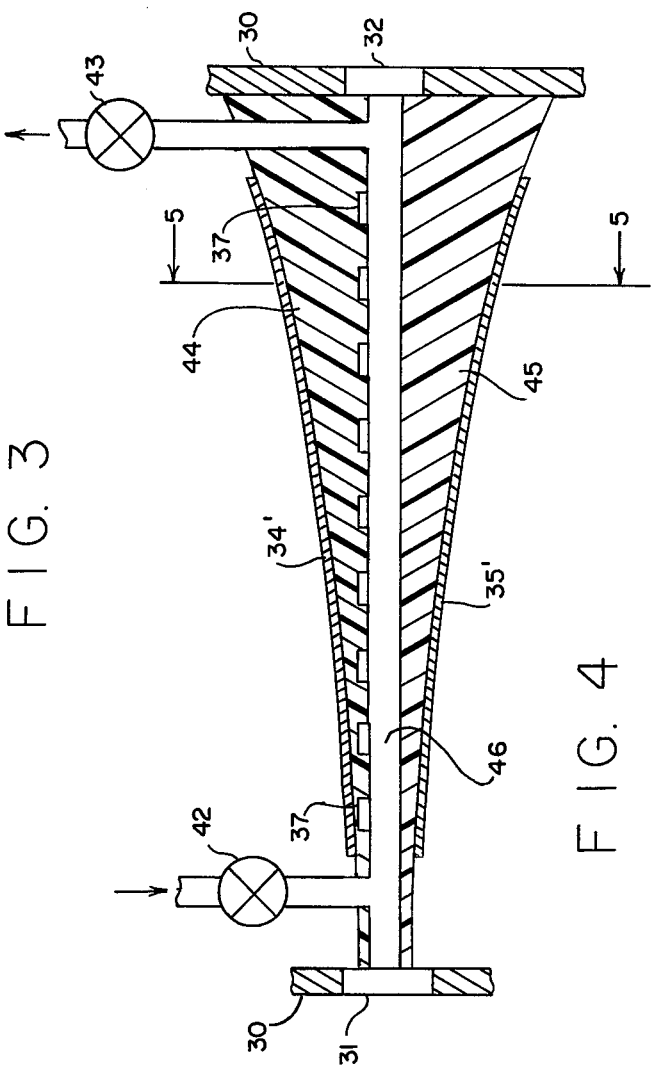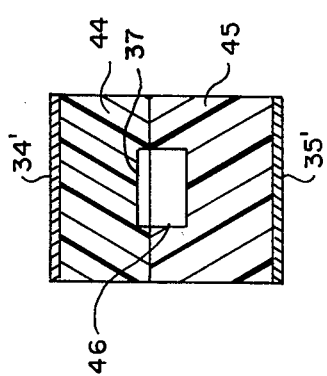

STARK EFFECT SPECTROPHONE FOR CONTINUOUS ABSORPTION SPECTRA MONITORING

ORIGIN OF INVENTION

The invention described herein was made in the performance of work under a NASA contract and is subject to the provisions of Section 305 of the National Aeronautics and Space Act of 1958, Public Law 85-568 (72 Stat. 435; U.S.C. 2457).

BACKGROUND OF THE INVENTION

This invention relates to a Stark effect spectrophone for continuous absorption spectra monitoring, and more particularly to a Stark effect spectrophone for continuous absorption spectra monitoring having divergent field electrodes, and methods of using it.

Spectrophones have become very promising for gas analysis in recent years. See "Laser Optoacoustic Spectroscopy—A New Technique for Gas Analysis by L. B. Kreuzer," Analytical Chemistry, Vol. 46, No. 2., February 1974 pp 239A–244A, and "Excited-State Spectroscopy of Molecules Using Opto-acoustic Detection" by C. K. N. Patel, et al., Physical Review Letters, Vol. 38, No. 21, May 1977, pp 1204–1207. Briefly, an optoacoustic detector or spectrophone operates by sensing pressure pulses induced in a gas sample by absorption of chopped laser radiation passing through it. The laser is tuned to different wavelengths to detect the presence of different constituent gases in the sample. Assuming that no energy is absorbed by the sample cell, the energy absorbed by the sample during each light pulse will increase the pressure of the gas in the sample cell in proportion to the amount of the absorbing gas present. This pressure pulse may be detected by a pressure transducer, hence the term optoacoustic detector for the sample cell and pressure transducer. The problem is that in practice the windows through which the laser beam passes through the cell will absorb some energy and introduce acoustical noise in the system.

To solve this problem, Jack S. Margolis and Michael S. Shumate devised a spectrophone as described in an application Ser. No. 938,297 filed Aug. 31, 1978. Briefly, a CW laser beam having a spectral line coincident with an absorption line of a constituent of a gas sample in a closed cell is directed through windows in the cell to interact with the absorbing constituents. The interaction between the laser and an absorbing constituent causes a pressure proportional to the absorption coefficient of a constituent. Many gases possess a dipole moment, and will consequently have absorption frequencies that will exhibit the Stark effect. The pressure is detected by a microphone while an electric field between two parallel plates is modulated to move the spectral absorption line in and out of coincidence with the laser line. This is accomplished by a DC power source biasing the plates while a modulating waveform generator modulates the bias.

This Stark cell modulation technique moves the absorption line of the absorbing constituent inside the cell across the laser spectral line of interest, producing a pressure increase due to heating, and alternately to a position away from the laser line. The difference in pressure between the ON and OFF condition indicates the presence of the constituent, and the amplitude of the peak indicates the quantity (parts per million) of the constituent. The presence of all constituents of interest may thus be detected and measured by varying the DC bias voltage because the electric field dependence of the microphone signal will be due to absorption of any resonating laser lines coincident with the gas constituents in the spectrophone cell at a specific field intensity. Alternatively, a multiline laser may be used to excite the spectrophone cell, in which case the electric field dependence of the composite response produces a composite absorption which is unique and therefore determines the combination of excited constituents in the spectrophone cell, i.e., produces a signature of the particular gas in the spectrophone cell.

Stark cell spectrophones in the prior art have had parallel plates to give a uniform electric field of a single value between the plates. When the cell is filled with a gas and it is desired to plot the absorption over a range of electric fields, it is necessary to keep changing the value of the voltage on the plates, and take discrete measurements of the microphone output for each value of the voltage on the plates. To plot absorption vs. electric field, the voltage on the plates can be swept simultaneously with readout of the microphone output. This procedure is satisfactory for a static (nonflowing and nonchanging) gas volume, but it is not fast enough for realtime detection of the constituents of a gas flowing through the cell. What is required is a spectrophone which allows realtime detection of the constituents of a gas, instead of sequentially setting various field intensities as is done in the prior art. Thus, in some applications, it would be advantageous to monitor a continuous flow of an unknown gas to determine its constituents, or to otherwise determine the presence of all constituents of interest simultaneously, instead of one at a time by varying the electric field. It is therefore an object of this invention to provide a gas monitoring system for realtime monitoring of a continuous gas flow to eliminate operational problems inherent in varying the field intensity across the plates of the spectrophone, and one which will provide an instantaneous plot of absorption vs. electrostatic field. For example, in monitoring a continuous flow of two or more gases, each of which absorb at the laser wavelength but at slightly different values of electric field strength, the relative concentrations of each gas could be continuously displayed in realtime. This requires an optoacoustic detector having the capability of determining energy absorptions at several field strength values simultaneously.

SUMMARY OF INVENTION

In accordance with the present invention, a Stark effect spectrophone is provided with a pulsed (P) or continuous wave (CW) laser for monitoring the constituents of an unknown gas. The laser beam is directed through windows of a closed cell while the unknown gas to be monitored is caused to flow continuously through the cell between electric field plates disposed in the cell on opposite sides of the beam path through the cell. The plates are so disposed as to be divergent, e.g., flat plates at an oblique angle relative to each other, or plates shaped according to a mathematical function, so that with constant voltage applied across the plates, there is a variation in electric field strength along the beam path. Discrete energy absorption sensors are positioned at field strength points of interest. When a beam is passed through the cell, energy absorbed by the gas then present in the cell will increase gas pressure and temperature at each point along the beam path according to the spectral lines of the constituents of the gas for the particular field strengths at those points. This increase is sensed at each point simultaneously while modulating the absorption of the beams energy by the gas sample in the cell. In one embodiment, the beam is pulsed (by using a pulsed laser or a CW laser and a chopper disc with narrow slots) to modulate absorption. In another embodiment, the electric field is modulated by adding a small AC signal to the DC bias voltage. Still other embodiments include modulating the wavelength or polarization of a CW laser that is not pulsed or chopped. Yet another embodiment employs a 50% duty cycle chopper.

In the pulsed mode, the absorption measurement at each point during each pulse of energy will yield a plot of absorption as a function of electric field for parallel detection of the gas constituents of interest, but it is preferable to repeat the pulses over a short time in order to obtain repeated energy absorption measurements for averaging before recording and processing the data, provided the time over which the pulses occur is short relative to the gas flow. In the modulated field mode, a constant illumination intensity is employed and the electric field voltage is dithered such that a continuous absorption spectrum is plotted over all the points of interest. As the voltage is dithered, the energy absorption at each point of interest will vary according to the slope of the absorption spectrum at the point of interest, thus yielding signature spectra for the constituent or constituents. Similarly, the rotating polarization mode and the wavelength modulation mode will each yield a signature spectra for the constituent or constituents. The 50% duty cycle chopper will also modulate energy absorption to yield signature spectra. The signature spectra in each case will indicate the presence of the sample gas constituents and the proportions of each.

The novel features that are considered characteristic of this invention are set forth with particularity in the appended claims. The invention will best be understood from the following description when read in connection with the accompanying drawings.

BRIEF DESCRIPTION OF THE DRAWINGS

FIG. 3 illustrates one arrangement for electric field plates for the system of FIG. 2.

FIG. 4 illustrates another arrangement for electric field plates for the system of FIG. 2.

FIG. 5 is a cross section taken on line 5—5 of FIG. 4.

DESCRIPTION OF PREFERRED EMBODIMENTS

Figure 1:
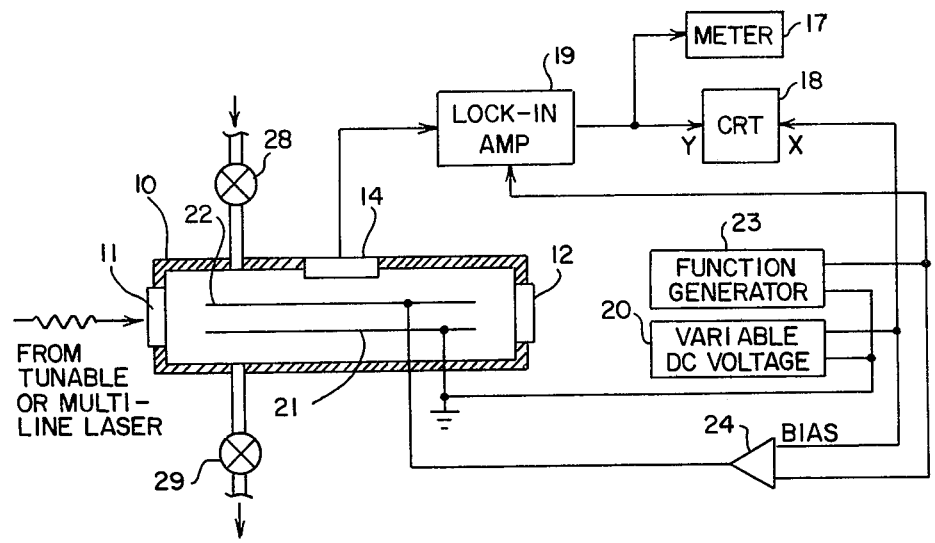
FIG. 1 is a block diagram of the prior art.

Referring first to the prior art shown in FIG. 1, a spectrophone cell 10 is provided with windows 11 and 12, e.g., ZnSe windows, at the opposite ends so that a beam from a tunable laser or multiline laser (not shown) can be directed through the cell. A pressure transducer (microphone) 14 is in communication with the gas in the cell 10. The gas within the cell can be excited by the laser beam if its absorption frequency (spectral line) is the same as the laser frequency (line). This excitation manifests itself as heat, causing the pressure in the cell to increase.

The magnitude of this change is proportional to the absorption of the sample at the laser frequency, and is a function of its absorption coefficient and quantity (parts per million). The presence of a constituent may thus be detected by a peak signal at the spectral line of the constituent if the laser is tuned across the spectral line, and the parts per million of the constituent may be determined from the amplitude of the peak. However, the true amplitude of the peak is obscured in that the baseline may shift due to increased pressure in the cell caused not by absorption of laser energy by the gas but by the windows at each end.

To overcome that window noise problem, a DC voltage from a source 20 is applied to parallel plates 21 and 22 in the cell 10 to produce an electric field at a voltage level adjusted to bias the spectral line of the gas constituent of interest onto the laser spectral line, i.e., to bias the center frequency of the absorption resonance of the constituent gas at the laser frequency, thus transforming the cell 10 into a Stark effect cell. A function generator 23 applies a periodic reference signal to the plates via a summing amplifier 24 to vary the spectral line (absorption resonance of the constituent gas) about the laser frequency. That effectively modulates the laser beam passing through the cell with respect to the spectral line. The presence of the constituent may thus be detected by a peak signal at the spectral line for the constituent, and the parts per million of the constituent determined from the amplitude of the pressure modulation peaks.

The effect of the bias modulation is to cause a modulated electric field to be created between the plates 21 and 22, the magnitude of which causes a reaction with polar molecular gases, such as water vapor, some atmospheric fluorocarbons, and some nitrous and nitric compounds of interest for detecting explosives, and many others having a dipole moment. It is thus possible to tune the spectral lines of gas constituents of interest across the laser spectral line and detect the constituents gases of the sample in the cell. But since it requires some time to sweep the entire line spectra of interest by varying the DC voltage source 20, it is necessary to hold the sample gas in the cell during this time. A continuous flow of gas is not possible.

Figure 2:
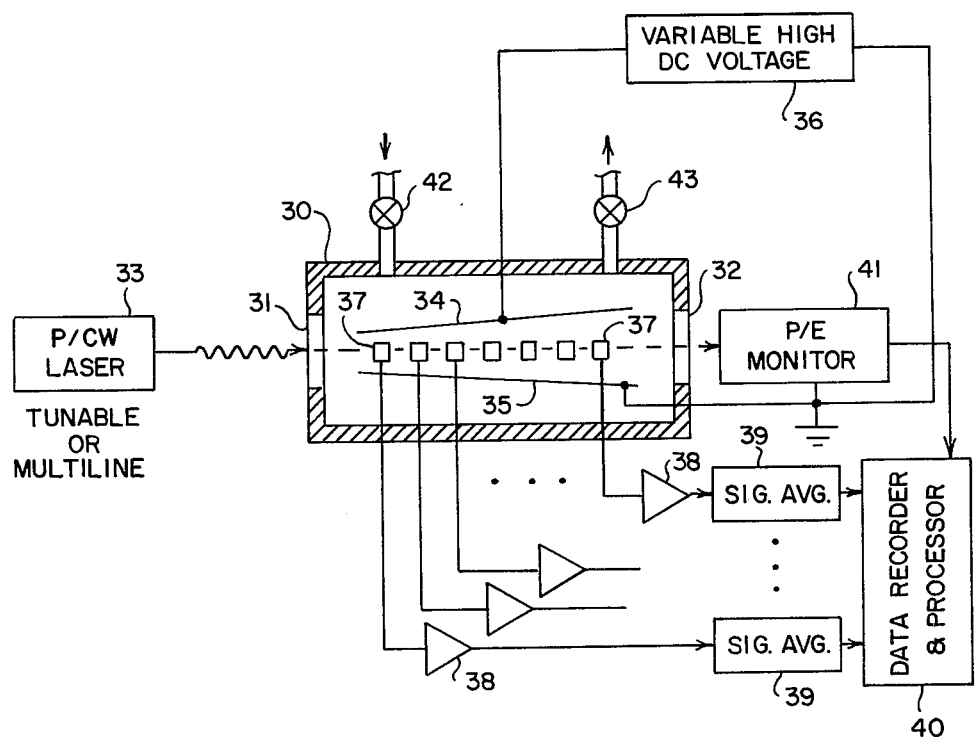
FIG. 2 is a block diagram of the present invention.

Referring now to FIG. 2, the limitations of the prior art are overcome by having a cell 30 with windows 31 and 32, as before, and a pulsed (P) or continuous wave (CW) laser 33 (tunable or multiline) with divergent electric field plates 34 and 35 connected to a source of high DC voltage 36. The voltage is preferably variable, in order to adjust the instrument for a particular group of gas constituents of interest, although in one embodiment it is not necessary to vary the voltage during use to monitor the constituents of a gas. In other embodiments, to be described hereinafter, a CW laser is used and other energy absorption modulation techniques are employed.

The divergent plates 34 and 35 provide a spacing along the length of the plates such that the electric field varies along the length. The electric field is an inverse function of the spacing. A plurality of pressure transducers 37 are positioned at points along the length of the plates to detect pressure increases during the presence of a laser pulse. These pressure increases are representative of the absorption of the laser beam by gas constituents at discrete values of the electric field. In that way the absorption spectra of a gas sample is obtained for all constituents of interest simultaneously.

Detector outputs are appropriately processed by amplifiers 38 and signal averagers 39 over a number of successive laser pulses to present to a data recorder and processor 40 (for display and/or analysis) the data required for an instantaneous plot of the absorption as a function of electric field. A power (P) or energy (E) monitor 41 is used to measure the intensity of the beam from pulse to pulse in order to normalize the data. This instantaneous plot capability will allow a gas having particular constituents to flow through the cell at a rate set by valves 42 and 43 while providing realtime plotting by virtue of discrete field point sampling. The resolution of the plot is dependent only on the length of the cell, the slope of the plates and the spacing of the pressure detectors. In that manner, detectors stationed at points of various field intensities will provide points of a plot of pressure along the ordinate and field intensity along the abscissa. The plot is made in realtime, since all field intensities are sampled simultaneously. No voltage adjustments need be made to vary the field intensity. The rate of gas flow is not important provided the gas is homogeneous and uniform in temperature, except for absorption heating.

The field plates may be flat as shown in greater detail in FIG. 3, or curved according to some mathematical function as shown in FIG. 4. Since the field strength is not a linear function of the spacing between the plates, flat plates with uniformly spaced detectors will not provide for a linear variation in electric field. For a linear variation in electric field, the plates must each describe a hyperbolic arc. In general, the angle between the electrodes determines the resolution of the instrument. For small angles between the plates, a relatively large number of microphones can be placed, each sampling at a unique field intensity point. The DC voltage applied to the plates determines the maximum and minimum electric field values; the maximum being where the plates are closest together, and the minimum being where the gap is largest.

To maintain the gas volumes constant along the diverging field plates, dielectric material can be placed in the spectrophone to compensate for the increased spacing between the plates. This is shown in FIG. 4, wherein reference numerals of elements common to the system of FIG. 2 are identified by the same reference numerals, and similar but distinct elements are identified by primed reference numerals. FIG. 4 also illustrates the use of shaped electrodes 34' and 35', as noted above. The dielectric material is provided in two parts (44, 45). Upon being joined, the two parts form a small channel 46 for the gas with the pressure transducers embedded in one part (44), as shown in FIG. 4 and in the transverse cross section of FIG. 5 taken on a line 5—5 in FIG. 4. The walls of the cell 30 thus serve only to hold the windows 31 and 32 and support the dielectric structure with embedded transducers and the field plates 34' and 35'. It should be noted that the transducers 37 may also be to the side of the electrodes as in FIG. 3.

In each of the arrangements for the plates illustrated, the fact that a single voltage level is used on the plates eliminates some of the problems inherent in using an adjustable voltage in the range of 0 to 1000 volts to vary the field intensity. As the voltage is varied in the prior art, physical properties may alter the operating conditions and the responsivities of the instrument. Yet the voltage source may be variable, not for varying the electric field during use, but for initially setting up the instrument for use in some particular application, i.e., for some particular group of gas constituents.

Modulating the absorption of the beam's energy may be achieved in still other ways, such as by polarization rotation, wavelength modulation, or conventional 50% duty cycle chipping. In each case, unique signature spectra for sample gas constituent or constituents may be plotted after calibration to identify the constituent or constituents and determine their proportions.

The invention is particularly applicable to realtime monitoring of a continuous gas flow; for example, to monitor a mixture of two gases, both being Stark modulated gases with an absorption line at or near the laser wavelength. The gases exhibit variations in absorption vs. electric field. If it is desired to monitor a flowing mixture of two gases; i.e., the ratio of the two gases, the electric field values could be set up to cover absorption peaks of both the gases and display the energy absorption sensor output on an oscilloscope, or any display device that would show the signal vs. the sensor position, i.e., the electric field. This would provide a continuous monitoring of a proportion of the two constituents in the gas flow.

As noted hereinbefore, a variant of the invention is to use thermocouples for sensing the energy absorbed at various field intensity points, in lieu of pressure transducers. Still other variations and equivalents will occur to those skilled in the art. Consequently, although particular embodiments have been described and illustrated herein, it is recognized that modifications and variations may readily occur to those skilled in the art. Therefore, it is intended that the claims be interpreted to cover such modifications and equivalents.

What is claimed is:

1. A method for gas analysis using the Stark effect comprising the steps of
   generating a beam having at least one predetermined spectral line frequency,
   placing a gas sample in a cell in the path of said beam, said cell having windows for said beam to pass, and two electric field plates disposed along said beam and diverging in respect to each other, one plate on each side of said beam to form an electric field that varies in intensity as a function of the distance between the plates along the length of the plates,
   applying a constant bias voltage to said plates to adjust the absorption lines of at least one of a plurality of predetermined constituents suspected to be present in said gas sample into coincidence with one of said beam spectral lines, and
   sensing absorbed energy variations of said gas in said cell at points along the length of said plates while modulating the absorption by said gas sample of the beam's energy.

2. The method of claim 1 wherein said gas sample contains a plurality of suspected constituents, each having a predetermined distinct absorption line, and simultaneously displaying the absorbed energy variation of all sensors, thereby to detect the presence of said plurality of constituents from the predetermined absorption lines and the proportions of the constituents.

3. The method of claim 1 wherein each of said plates is flat and placed at a small angle with respect to the beam axis.

4. The method of claim 1 wherein said plates are shaped so that with a constant bias voltage applied across the plates, there is a variation in electric field strength along the beam path that is linear.

5. Apparatus for gas analysis using the Stark effect comprising
   means for generating a beam having at least one predetermined spectral line frequency, a gas sample cell in the path of said beam, said cell having windows for said beam to pass, and electrically isolated plates disposed on opposite sides of said beam and diverging with respect to each other to form an electric field which varies, means for applying a constant bias voltage to said plates to create an electric field between said plates which will adjust the absorption line of a predetermined constituent suspected to be present in said gas sample into coincidence with said laser spectral line at one of a plurality of distinct points along said beam path, means for modulating the absorption by said gas sample of the beam's energy, means for separately sensing absorbed energy variations of said gas in said cell at said distinct points, while modulating the absorption of the laser's energy by said gas sample, and means for displaying said absorbed energy variations at distinct points.

6. Apparatus as defined in claim 5 wherein each of said plates is flat and placed at a small angle with respect to the beam axis.

7. Apparatus as defined in claim 5 wherein said plates are shaped so that with a constant bias voltage applied across the plates, there is a variation in electric field strength along the beam path that is linear, and said sensors are evenly spaced.

8. Apparatus as defined in claim 5 wherein said electrically isolated plates are covered with a dielectric material forming opposing walls of said cell, whereby said plates are isolated from each other by side walls of dielectric material.

9. Apparatus as defined in claim 8 wherein said dielectric material forms a channel of a minimum dimension necessary to pass said laser beam, thereby to form a minimum volume of gas that is of uniform dimensions along the path of said beam through said laser.

10. Apparatus as defined in claim 5 wherein said means for modulating the absorption by said gas sample of the beam's energy is comprised of means for producing beam pulses, where the pulses are short as compared to the time between pulses, and including means for averaging the energy absorption sensed of a number of pulses at each point along said electric field, where the time required for said number of pulses is small considering the rate at which gas flows through said cell.

* * * * *